United States Patent [19]

Snyder

[11] Patent Number: 4,926,963
[45] Date of Patent: May 22, 1990

[54] SOUND ATTENUATING LAMINATE FOR JET AIRCRAFT ENGINES

[75] Inventor: Stephen J. Snyder, West Hills, Calif.

[73] Assignee: UAS Support, Inc., Geneva, Switzerland

[21] Appl. No.: 333,346

[22] Filed: Apr. 5, 1989

Related U.S. Application Data

[63] Continuation-in-part of Ser. No. 106,618, Oct. 6, 1987, Pat. No. 4,848,514.

[51] Int. Cl.$^5$ .............................................. E04B 1/82
[52] U.S. Cl. ................................... 181/290; 181/213;
181/214; 181/222; 181/286; 181/293; 181/294;
428/138; 428/246; 428/251; 428/284; 428/285;
428/450; 428/458; 428/466; 428/920; 244/1 N
[58] Field of Search ............... 181/213, 214, 222, 290,
181/292, 293, 294, 286; 29/525.1, 525.2; 244/1
N, 53 B; 428/138, 246, 251, 284, 285, 450, 458,
466, 920

[56] References Cited

U.S. PATENT DOCUMENTS

| | | | |
|---|---|---|---|
| 2,081,952 | 6/1937 | Parkinson | 181/286 |
| 2,326,763 | 8/1943 | Crandell | 181/293 |
| 2,674,335 | 4/1954 | Lemmerman | 181/222 X |
| 2,674,336 | 4/1954 | Lemmerman | 181/222 |
| 3,542,152 | 11/1970 | Adamson et al. | 181/222 |
| 3,710,890 | 1/1973 | True et al. | 181/222 |
| 3,712,846 | 1/1973 | Daniels et al. | 428/138 |
| 3,748,213 | 7/1973 | Kitching et al. | 428/138 |
| 4,056,161 | 11/1977 | Allen, Jr. | 181/294 X |
| 4,130,175 | 12/1978 | Hehmann | 181/290 |
| 4,137,992 | 2/1979 | Herman | 181/213 |
| 4,313,524 | 2/1982 | Rose | 181/222 X |
| 4,441,578 | 4/1984 | Rose | 181/222 |
| 4,488,619 | 12/1984 | O'Neill | 181/290 |
| 4,567,092 | 1/1986 | Catrain | 428/246 |
| 4,759,513 | 7/1988 | Birbragher | 181/222 X |
| 4,838,380 | 6/1989 | Lassiter | 181/294 X |
| 4,848,514 | 7/1989 | Snyder | 181/290 |

FOREIGN PATENT DOCUMENTS 984817 3/1961 United Kingdom .

OTHER PUBLICATIONS

Woodall, J., Quieting the JT3D Powered 707, Feb., 1974, Acoustical Publications Inc., pp. 20-25.

*Primary Examiner*—Benjamin R. Fuller
*Attorney, Agent, or Firm*—Kenyon & Kenyon

[57] ABSTRACT

The present invention relates to a novel sound attenuating laminate. More particularly, the invention relates to a simpler, lighter, and more effective noise attenuating laminate which is made up of seven layers of material. The laminate includes a duct liner, a moisture barrier, a first protecting layer, a screen, acoustic attenuating material, a second protecting layer, and a solid backing sheet. The laminate is readily incorporated into various sections of a jet engine compartment in order to attenuate the sound produced by the jet engine. Hollow rivets are used to conduct acoustical energy to the intermediary layers of the noise attenuating laminate.

25 Claims, 4 Drawing Sheets

SOUND ATTENUATING LAMINATE FOR JET AIRCRAFT ENGINES

This application is a continuation-in-part of U.S. Ser. No. 106,618, filed October 6, 1987, U.S. Pat. No. 4,848,514 and entitled Sound Attenuation System for Jet Aircraft Engines.

The present invention relates to the field of sound attenuation, and more particularly to a sound attenuating laminate which can be used for the suppression of sound produced by jet aircraft engines.

BACKGROUND OF THE INVENTION

The method presently in use for attenuating noise generated by the commercial jet aircraft engines was initially developed in the late 1960's and early 1970's by the manufacturers of such aircraft. This technology consists of an acoustic lining system for the engine, having a sandwich-type construction consisting of sintered metal mesh facing the engine air flow paths in the inlet and fan exit ducts. This mesh is bonded to the duct liner skin with a precisely sized and spaced hole pattern tuned to the primary noise frequency generated in that portion of the engine at the critical operating mode being silenced. The metal mesh and perforated duct liner skin are bonded to a honeycomb structure backed with a solid skin.

At the time this system was developed, the industry objective was to meet the requirements of Federal Air Regulation Part 36, Stage 2. This system remains the primary industry development for attenuating the noise generated by narrow-bodied jets, as it has been perceived as the only system adequate for service in its unique operating environment in the jet engine. For example, JT3D commercial jet engines installed on Boeing 707 and DC8 aircraft have used and continue to use this system.

Sound attenuation with this system is accomplished by the Helmholz Resonator effect whereby cavities in the honeycomb dissipate acoustical energy after its admittance through the metal mesh and perforated skin which has been placed between the honeycomb and the sound generating elements of the engine. The solid skin backing in the honeycomb is impervious to acoustical energy radiation and prevents acoustical transmission. Some structure-borne sound transmission is transmitted by the sandwich construction, but this is of a secondary nature. Loss in engine performance, however, has been associated with air leakage through the honeycomb lining.

The noise generated by the fan section of jet engines occurs at discrete primary frequencies which vary depending on engine model, fan speed, and location along the duct. Attenuation of such noise using the above mentioned method has the potential to achieve the initial goal of and compliance With Stage 2 of the Federal Air Regulations, Part 36. Therefore, industry research has concentrated on the precise tuning of the lining design to the engine noise source characteristics, with emphasis on acoustic parameters of different dimensional and material properties of the porous metal facing sheet, honeycomb core, and the solid backing sheet. Results have been barely adequate with differing degrees of economic and operational penalties.

The system described above is estimated to be capable of producing an attenuation of 6 to 11 DB and requires the meticulous fine tuning of critical parameters such as skin hole size, metal mesh grid and thickness, honeycomb material makeup, and cavity dimension and thickness. This system is designed to attenuate only one primary frequency for a given combination of critical parameters. The result has been marginal compliance with the Stage 2 requirements of Federal Air Regulations, Part 36. Moreover, Stage 3 requirements have not yet been reached with the present system without resort to measures which result in a high cost and high risk solution to the noise problem and a significant engine performance penalty, exposure to catastrophic engine failure, and continuing maintenance problems. A further problem with such measures would involve obtaining airframe and engine manufacturer approval for the attendant inlet airflow changes.

SUMMARY OF THE INVENTION

It is, therefore, an object of this invention to provide a straightforward, well-constructed noise attenuating laminate for various jet aircraft engines which allows for more efficient attenuation of sOund energy.

It is a further object of this invention to provide a noise attenuating laminate for jet aircraft engines which would comply with Stage 3 of the Federal Air Regulations, Part 36 noise attenuation requirements with minimal economic and operational penalties.

It is yet a further object of this invention to provide a sound attenuating laminate which would achieve non-linear acoustic attenuation over a broad range of noise frequencies without the need for any fine tuning requirements.

It is another object of this invention to provide for a sound attenuating laminate which would prevent loss of engine performance associated with air leakage.

The objects of this invention are accomplished by providing a sound attenuating laminate which consists of a number of layers. The first layer is a fan inlet duct and center body liner, fan exhaust duct inner and outer liner, and engine access door liner. These liners are perforated to allow for the entry of acoustic energy and can consist of aluminum or stainless steel. The second layer is a moisture barrier which is located next to the perforated liner and can be made up of fiberglass fabric or fire resistant ceramic fabric. This layer is saturated with pressure sensitive silicone adhesive and thus bonded to the liners above. The third layer consists of fiberglass coated with either silicone rubber, viton, fluourosilicone, or teflon. This layer protects the fourth and fifth layers from moisture, fluids, and other contaminants and serves as a membrane for the passage of acoustic energy to the acoustic attenuating material. The fourth layer consists of a screen of plastic, such as polypropylene, or stainless steel. This screen serves as a spacer to separate the third layer from the acoustic attenuating material of the fifth layer. This screen also provides a fill air space to allow for the passage of acoustic energy to the acoustic attenuating material. The fifth layer consists of acoustic attenuating material such as fiberglass or ceramic fiber blanketing. The sixth layer can be made up of any of the same materials as the third layer. The seventh and last layer is a solid backing sheet which may be the outer skin of the nose cowl. This layer reflects any acoustic energy which has passed through the preceding layers back towards the acoustic attenuating material.

In installing the laminate, hollow rivets are utilized to replace certain solid structural rivets at certain locations of the jet engine, most particularly the inlet duct and the nose cone. These hollow rivets penetrate anti-icing airflow channels to achieve an improved anti-icing system and allow for the passage of acoustic energy radiation from its origin, through the duct liner or nose cone outer skin, and to the acoustic attenuating material.

DETAILED DESCRIPTION OF A PREFERRED EMBODIMENT

Figure 1:
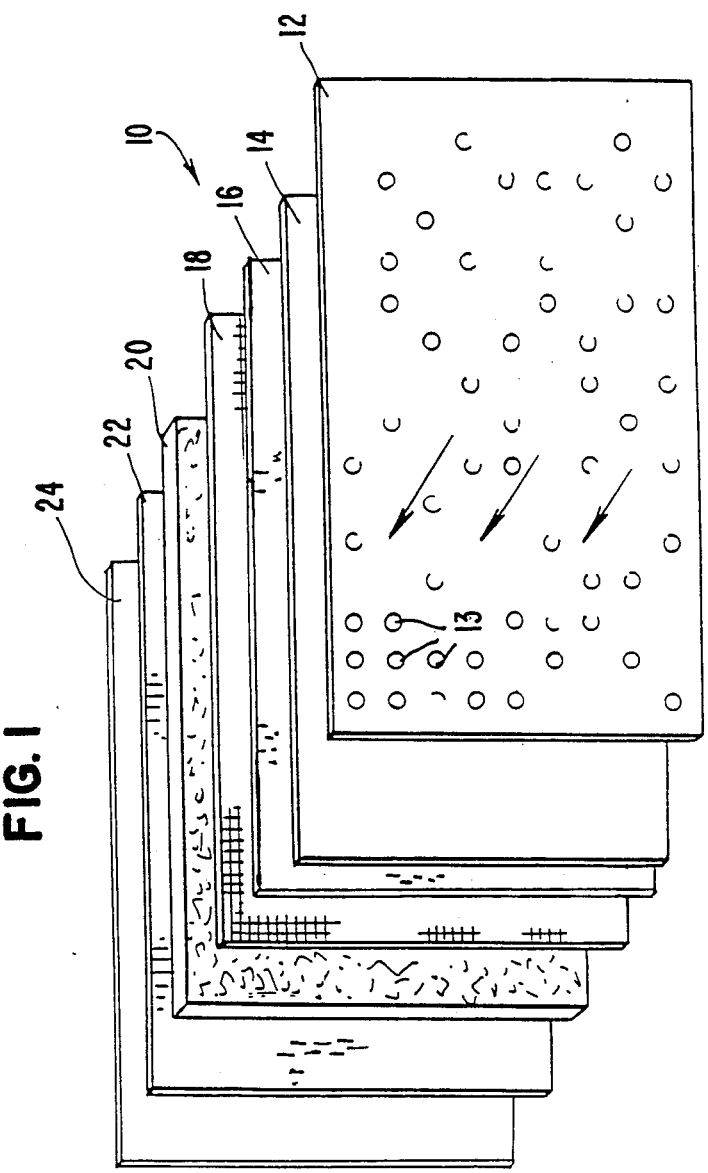
FIG. 1 is a schematic diagram showing the seven layers making up an embodiment of the sound attenuating laminate described in the present invention.

Referring specifically to the drawings, FIG. 1 illustrates one embodiment 10 of the present invention. According to this invention, the sound attenuating laminate has seven layers as can be seen in FIG. 1. The first layer 12 is a liner which may be a fan inlet duct liner, a center body liner, a fan exhaust duct liner, or an access door liner. This liner 12 can consist of aluminum or stainless steel and contains perforations 13 that allow for the entry of acoustic energy. The perforations 13 are preferably about one-eighth of an inch in diameter and spaced at approximately five-sixteenth of an inch intervals along the liner.

The second layer 14 of the sound attenuating laminate is composed of a moisture barrier. This moisture barrier 14 is adjacent to the liner 12. A suitable moisture barrier material was found to be fiberglass fabric or fire resistant ceramic fabric. These fabrics are saturated with pressure sensitive silicone adhesive such as PSA 52 with SRC 18 catalyst, manufactured by the General Electric Company, Silicone Products Division, Waterford, N.Y., and are thereby made to bond to the liner 12.

The third layer 16 is a protecting layer and can be composed of fiberglass fabric coated with silicone rubber, viton, fluorosilicone, or teflon. This layer protects the fourth and fifth layers from vapor, moisture, fuel, hydraulic fluid, engine oil, and other contaminates which would be hazardous if allowed to collect and which would also detract from the performance of the acoustic attenuating material. The third layer 16 also serves as a gas permeable membrane allowing for the passage of acoustic energy to acoustic attenuating material in the fifth layer 20. Acoustical energy is carried by air molecules which impinge on the gas permeable membrane 16 causing it to vibrate at the frequency of the acoustical energy being carried. As the gas permeable membrane 16 vibrates, it in turn energizes air molecules on its other side, directing them to the acoustic attenuating material.

The fourth layer 18 consists of a screen of stainless steel or plastic, such as polypropylene, with openings of approximately one eighth of an inch which serves as a spacer to separate the third layer 16 from the fifth layer 20 while maintaining an air space between the third and fifth layers so as to allow the fiberglass coated fabric of the third layer 16 to perform as a membrane in allowing acoustic energy to pass through to the acoustic attenuating material of the fifth layer 20.

The acoustic attenuating material in the fifth layer 20 is formed in a blanket type configuration, preferably two inches thick and is adjacent to the screen of the fourth layer 18. One suitable sound attenuating material was found to be Kaowool ceramic fiber blanketing, manufactured by the Insulating Products Division of Babcock and Wilcox, a McDermott company. Another suitable acoustic attenuating material was found to be 1000 Series Spin-Glas Fiber Glass Insulation, manufactured by the Manville Building Materials Corporation, a subsidiary of the Manville Corporation, Ken-Caryl Ranch, P.O. Box 5108, Denver, Colo. 80217. As discussed below, such materials are appropriate for use in different portions of the engine.

The sixth layer 22 is also a protecting layer and can be made up of the same materials as the third layer 16. The surface of the sixth layer 22 facing away from the acoustic attenuating material of the fifth layer 20 may be additionally coated with aluminum foil to serve as a radiation heat shield where elevated temperatures make this necessary.

The seventh layer 24 is a solid backing sheet which can be composed of aluminum or titanium and which may actually be the outer skin of the nose cowl, fan ducts, or cowl doors, or the inner surface of the nose cowl. It serves to reflect any acoustic energy which has passed through the preceding layers back towards the acoustic attenuating material in the fifth layer 20.

As one can see from the previous discussion, a number of variations are permitted in the construction of the novel laminate. For example, a fire resistent layer could be added to the sound attenuating laminate between the second layer 16 and the third layer 18 in order to protect the acoustic attenuating material and the external aircraft structure from fire hazards. A suitable fire barrier was found to be Nextel 312 Woven Fabric, manufactured by the Ceramic Materials Department of the 3M Corporation, Building 225-4N-07, 3M Center, St. Paul, Minn. 55144-1000. Furthermore, the third layer 16 and sixth layer 22 of the sound attenuating laminate could be fused together at their edges by heat (vulcanized), or by bonding with an adhesive such as PSA52 with SRC 18 catalyst manufactured by the General Electric Company, Silicone Products Division, Waterford, N.Y., thereby encapsulating the fourth 18 and fifth layer 20 further protecting them from vapor, moisture, fuel, hydraulic fluid, engine oil, and other contaminants.

Figure 2:
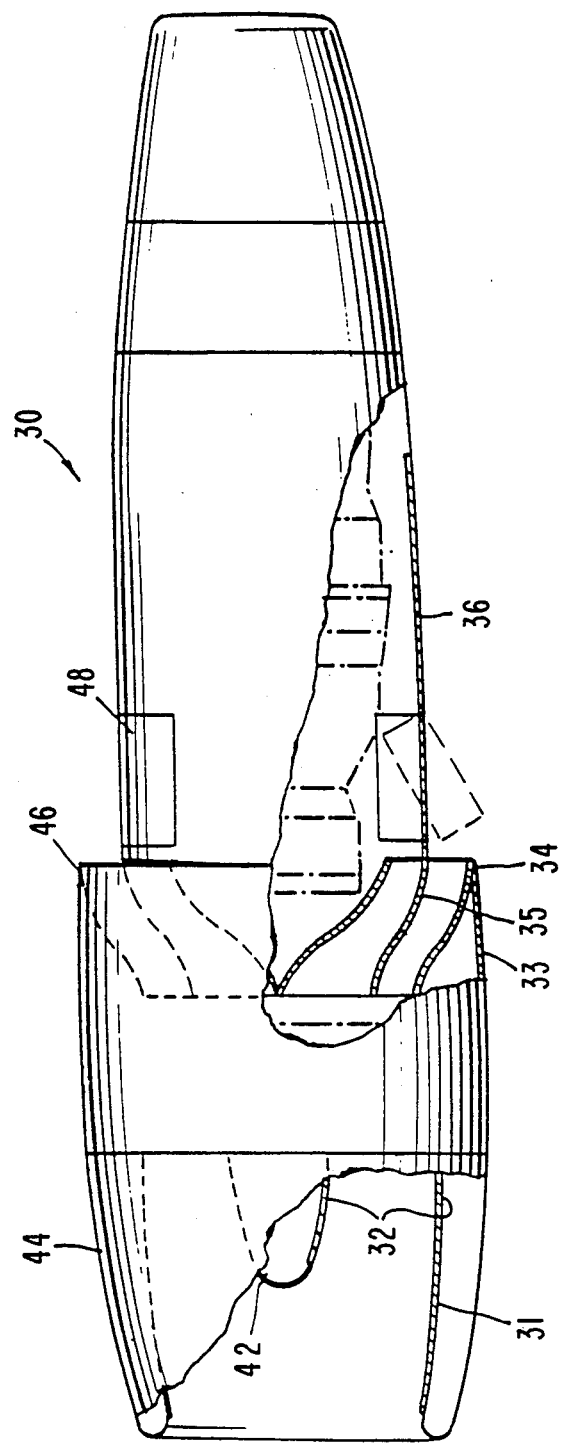
FIG. 2 is a diagram showing a jet engine nacelle indicating where the sound attenuating laminate described in this invention would be placed within such a jet engine nacelle.

The resulting laminate is incorporated into various portions of the jet engine compartment. FIG. 2 shows a typical jet engine nacelle 30, such as that used to house the commercial model JT3D jet engine. Shaded areas 31-36 show the application of the laminate of the present invention. Primary areas for application include the fan inlet duct 44, the nose dome 42, the fan exhaust ducts 46 and access doors to the nacelle which envelop the engine around its circumference from the nose cowl aft to the exhause duct.

In the more forward areas of the engine, it is preferred to employ a fiberglass material as the acoustic attenuating material of the fifth layer 20, (e.g., areas 31, 32), while in more rear-ward areas, such as areas 34, 35 and 36, it is preferred to use the ceramic fiber material. The fiberglass material, however, is a superior sound attenuating material which is substantially lighter in weight. The ceramic fiber material is used adjacent to hot areas of the engine as it will withstand temperatures in excess of 2000° F.

The sound attenuating laminate of the invention incorporates the existing air flow liner in all areas except the access doors. The solid backing sheet can be the outer skin of the nacelle. For example, the inner surface of the access door outer skin serves as the backing sheet in that location. A perforated sheet of aluminum or stainless steel will face the engine, with the other layers of the sound attenuating laminate being placed between the perforated sheet and the inner surface of the outer skin. The perforated sheet will be mechanically fastened to the adjacent structure of the door.

Figure 3:
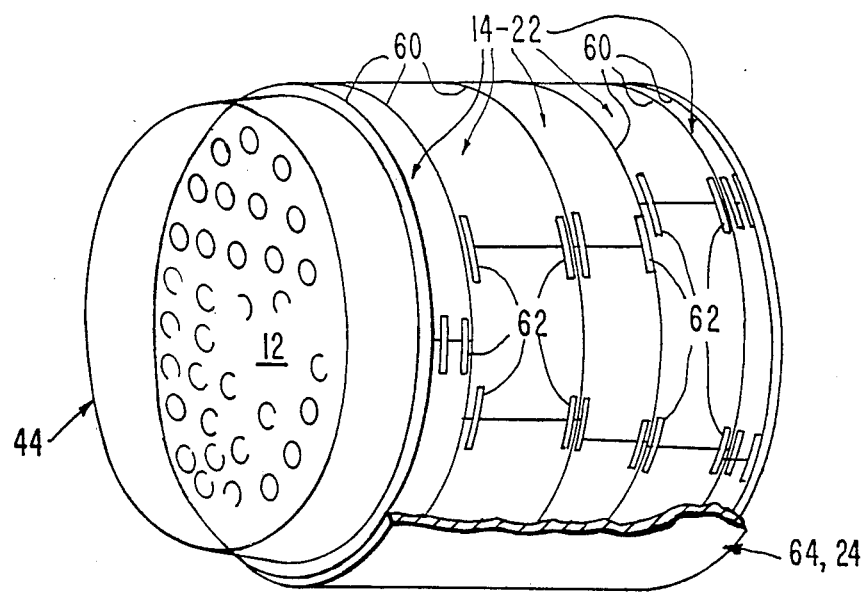
FIG. 3 is a diagram showing the installation of the sound attenuating laminate in the air inlet duct area of a jet engine nacelle.

For example, FIG. 3 shows the installation of the sound attenuating laminate 10 in the air inlet duct area of a jet engine nacelle. The intermediary layers of laminate 10 are installed around the air inlet duct 44, between its structural ribs 60. Once wound, the intermediary five layers 14-22 of the laminate are secured with velcro tapes 62. The perforated layer 12 is installed inside the inlet duct 44 and the outer skin 64 of the inlet duct 44 acts as the solid backing layer 24.

Figure 4:
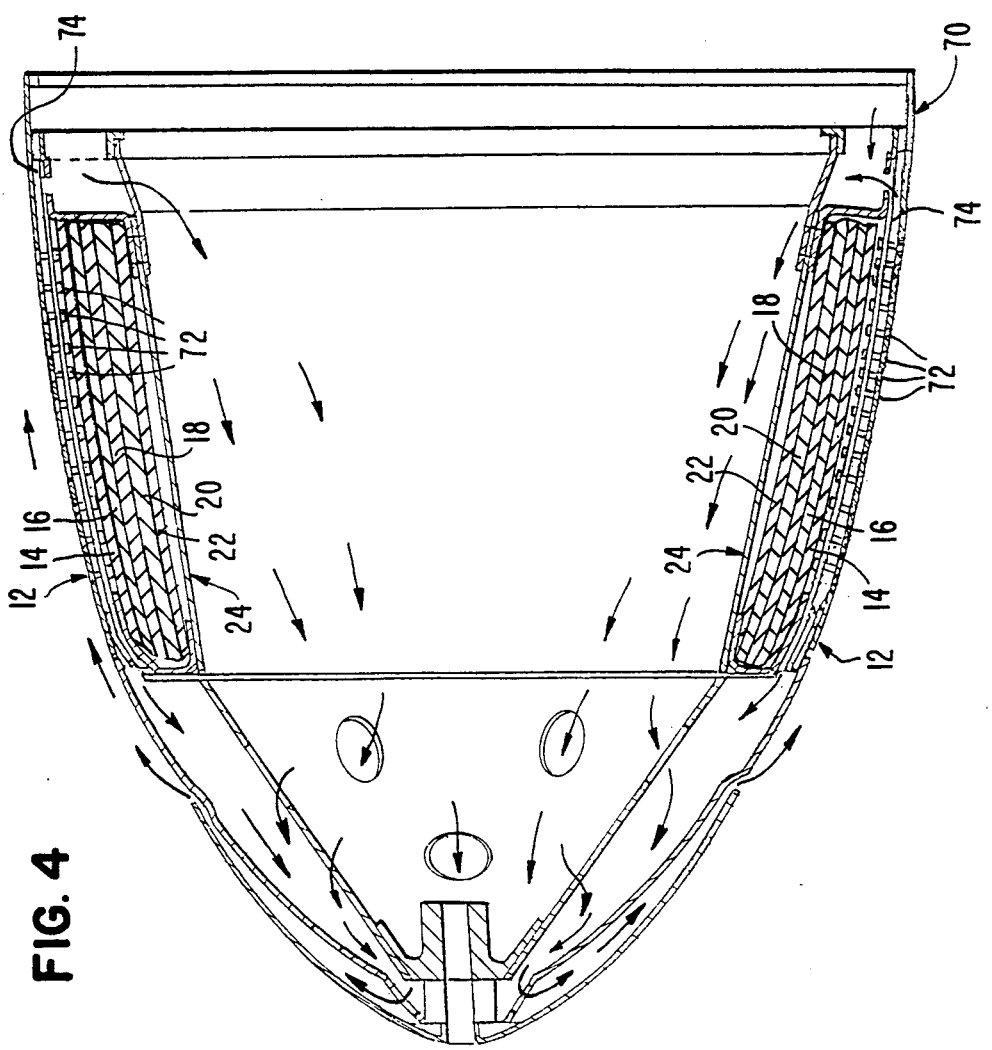
FIG. 4 is a diagram showing the installation of the sound attenuating laminate in the nose dome area of a jet engine.

FIG. 4 shows the installation of the sound attenuating laminate in the nose dome area of a jet engine. The laminate is installed within the nose bullet aft section 70, with hollow rivets 72 allowing the acoustic energy impinging on the nose cone to enter the intermediary layers 14-22 of the sound attenuating laminate.

Figure 5:
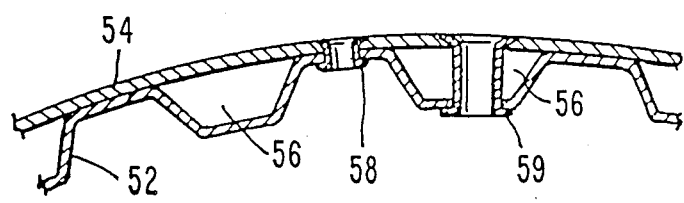
FIG. 5 is a diagram showing the use of hollow rivets to allow for the passage and attenuation of acoustical energy and to improve the anti-icing system.

The fan inlet duct areas are equipped with an anti-icing system, consisting of channels in the underside of each such structure through which hot air flows during anti-icing system operation. Such channels are composed of corrugations formed by the riveting of an inner liner to the inner wall of the fan duct inlet. This inner liner has been upset to form corrugated channels on the back surface of the inlet liner. When installing the laminate of the present invention, the existing solid rivets will be replaced with hollow rivets, and additional hollow rivets added as shown in FIG. 5. As seen there, the anti-icing channels 56 are formed by corrugated sheet 52 abutting a wall 54, which could be the wall of the fan inlet duct.

Conventionally, rivets have been placed at positions such as 58, where the corrugated sheet makes contact with the wall. In the present invention, however, not only are the rivets 58 replaced by hollow rivets, but additional hollow rivets 59 are inserted through channels 56. These rivets act as a novel means for providing conduits in the duct liner for the passage of acoustic energy generated by the jet engine through the wall of the fan duct or nose dome to the sound attenuating laminate. Furthermore, these hollow rivets will serve as acoustic horns which will not only strengthen the anti-icing duct nacelle through structural support, but will also act as efficient and easily installed conduits for conducting acoustic energy.

The duct liner and an inner liner will be riveted together to form a structurally stiff corrugated structure. This structure will also form the air flow passages for the flow of hot anti-icing air from the cowling inlet lip along the length of the inlet duct. The hollow rivets will function primarily for the passage of acoustic energy radiation. The rivets will also intersect the air flow passage at a right angle to the flow, and thus will also function as heat exchange baffles to improve the efficiency of the anti-icing systems of the inlet duct.

For example, the nose dome 42 of the engine normally has inserts attached to the dome's inner surface forming anti-icing air flow channels. These channels will be replaced in the present design. As shown in FIG. 4, the aft section 70 of the nose dome will be perforated to allow passage of acoustic energy to the sound attenuating laminate installed in the center of the dome's aft section 70. Hollow rivets 72 will be installed through the anti-icing channels 74 of the nose dome.

Efficiency of the jet engine anti-icing system will be improved in two ways. First, the hot air impinging on the outer surface of the hollow rivet will readily transmit heat to the duct liner outer skin. Second, the hollow rivets penetrating the anti-icing air passages will slow air flow through the passages, thus allowing for the transfer of more of the heat content of the hot air to the metal surfaces. The improvement in the anti-icing system efficiency may allow the jet engine anti-icing system to operate at reduced amounts of hot anti-icing bleed air, thus reducing the amount of engine air bled off for this purpose. Engine thrust may therefore be increased and fuel efficiency improved during anti-icing system operation.

The sound attenuating system of this design has been demonstrated to attenuate a broad range of noise frequencies without special fine tuning. It is estimated that attenuations of up to 23 DB may be possible based on previous experimental work. Furthermore, this system meets the primary requirements for fire and heat resistance imposed by the Federal Aviation Administration. This laminate system will be sealed from the engine air flow using the moisture barrier lamination to prevent the 2% loss in engine performance associated with the older sandwich type construction. The system will also be sealed from moisture and liquids, another significant problem inherent with the older sandwich-type construction.

In the foregoing specification, the invention has been described with reference to a specific exemplary embodiment thereof. It will, however, be evident that various modifications and changes may be made thereunto without departing from the broad spirit and scope of the invention as set forth in the appended claims. The specification and drawings are accordingly to be regarded in an illustrative rather than in a restrictive sense.

What is claimed is:

1. A multilayered laminate having improved sound energy attenuating properties comprising:
    a perforated facing layer;
    a moisture barrier layer adjacent to said facing layer;
    a first protecting layer adjacent to said moisture barrier layer;
    a screen layer adjacent to said first protecting layer;
    an acoustic attenuating material layer adjacent to said screen layer;
    a second protecting layer adjacent to said acoustic attenuating material layer; and
    a solid backing sheet layer adjacent to said second protecting layer.

2. The article of claim 1, wherein the perforations in said facing layer are comprised of a plurality of hollow rivets disposed throughout said facing layer.

3. The article of claim 1, wherein said perforated facing layer is composed of aluminum.

4. The article of claim 1, wherein said perforated facing layer is composed of stainless steel.

5. The article of claim 1, wherein said moisture barrier layer is composed of fiberglass fabric saturated with pressure sensitive silicone adhesive.

6. The article of claim 1, wherein said moisture barrier layer is composed of fire resistant ceramic fabric saturated with pressure sensitive silicone adhesive.

7. The article of claim 1, wherein said first protecting layer is composed of silicone coated fiberglass fabric.

8. The article of claim 1, wherein said first protecting layer is composed of viton coated fiberglass fabric.

9. The article of claim 1, wherein said first protecting layer is composed of fluorosilicone coated fiberglass fabric.

10. The article of claim 1, wherein said first protecting layer is composed of a teflon coated fiberglass fabric.

11. The article of claim 1, wherein said screen layer is composed of stainless steel.

12. The article of claim 1, wherein said screen layer is composed of polypropylene.

13. The article of claim 1, wherein said acoustic attenuating material layer is composed of ceramic fiber blanketing.

14. The article of claim 1, wherein said acoustic attenuating material layer is composed of fiber glass blanketing.

15. The article of claim 1, wherein said second protecting layer is composed of silicone coated fiberglass fabric.

16. The article of claim 1, wherein said second protecting layer is composed of viton coated fiberglass fabric.

17. The article of claim 1, wherein said second protecting layer is composed of fluorosilicone coated fiberglass fabric.

18. The article of claim 1, wherein said second protecting layer is composed of teflon coated fiberglass fabric.

19. The article of claim 1, wherein said second protecting layer is coated with aluminum foil.

20. The article of claim 1, wherein said solid backing sheet layer is composed of aluminum.

21. The article of claim 1, wherein said solid backing sheet layer is composed of titanium.

22. The article of claim 1, wherein said first protecting layer and second protecting layer each define its corresponding first edge and second edge, said first and second protecting layers being fused to each other at said first and second edges for encapsulating said screen layer and said acoustic attenuating material layer.

23. A multilayered laminate having improved sound energy attenuating and flame retardant properties comprising:
a perforated facing layer;
a moisture barrier layer adjacent to said facing layer;
a fire resistant layer adjacent to said moisture barrier layer;
a first protecting layer adjacent to said fire resistant layer;
a screen layer adjacent to said first protecting layer;
an acoustic attenuating material layer adjacent to said screen layer;
a second protecting layer adjacent to said acoustic attenuating material layer; and
a solid backing sheet layer adjacent to said second protecting layer.

24. The article of claim 23, wherein said fire resistant layer is composed of woven ceramic fabric.

25. The article of claim 23, wherein said first protecting layer and second protecting layer each define its corresponding first edge and second edge, said first and second protecting layers being fused to each other at said first and second edges for encapsulating said screen layer and said acoustic attenuating material layer.

* * * * *